US008597878B2

(12) United States Patent
Hillebrand et al.

(10) Patent No.: US 8,597,878 B2
(45) Date of Patent: Dec. 3, 2013

(54) DEVICE AND PROCEDURE FOR AUTOMATED ISOLATION AND PURIFICATION OF NUCLEIC ACIDS FROM COMPLEX STARTING MATERIALS OF THE USERS CHOICE

(75) Inventors: Timo Hillebrand, Hoenow (DE); Matthias Arndt, Berlin (DE); Uwe Wellnitz, Berlin (DE); Klaus Berka, Jena (DE); Volker Hillebrand, Rosslau/Elbe (DE)

(73) Assignees: AJ Innuscreen GmbH, Berlin (DE); AJ Cyberton Gesellschaft fuer Laborautomationssysteme Mbh, Berlin (DE)

( * ) Notice: Subject to any disclaimer, the term of this patent is extended or adjusted under 35 U.S.C. 154(b) by 976 days.

(21) Appl. No.: 12/115,766

(22) Filed: May 6, 2008

(65) Prior Publication Data
US 2009/0069555 A1   Mar. 12, 2009

Related U.S. Application Data

(63) Continuation of application No. PCT/EP2006/068147, filed on Nov. 6, 2006.

(30) Foreign Application Priority Data

Nov. 6, 2005 (DE) .................. 10 2005 053 463

(51) Int. Cl.
- *B01D 35/06* (2006.01)
- *B01D 15/08* (2006.01)
- *C12Q 1/68* (2006.01)
- *C12M 1/40* (2006.01)
- *C12M 1/42* (2006.01)

(52) U.S. Cl.
USPC ...... 435/6.1; 210/198.2; 210/223; 210/321.6; 210/498; 210/650; 210/656; 210/695; 210/767; 422/527; 422/534; 422/922; 435/288.6; 435/287.2; 435/287.7; 436/86; 436/161; 436/177; 436/501; 366/273

(58) Field of Classification Search
USPC .............. 210/198.2, 223, 263, 266, 498, 499, 210/143, 321.6, 638, 650, 656, 695, 767; 422/100, 101, 102, 501, 509, 513, 422/521–524, 527, 534, 535, 919, 922, 63, 422/105; 73/864.01; 435/6, 287.1, 287.2, 435/287.3, 287.6, 287.7, 288.1, 288.2, 6.1, 435/288.6; 436/86, 161, 177, 178, 501; 366/273

See application file for complete search history.

(56) References Cited

U.S. PATENT DOCUMENTS 4,059,020 A * 11/1977 Avakian ...................... 73/863.25
4,999,164 A *  3/1991 Puchinger et al. ............ 422/100

(Continued)

FOREIGN PATENT DOCUMENTS

| DE | 198 34 584 | 2/2000 |
| EP | 0941766 | 9/1999 |

(Continued)

OTHER PUBLICATIONS

Michael K. Hourfar, et al., "High-Throughput Purification of Viral RNA Based on Novel Aqueous Chemistry for Nucleic Acid Isolation", Clinical Chemistry 51:7, (2005), 1217-1222.

*Primary Examiner* — Joseph Drodge
(74) *Attorney, Agent, or Firm* — Oblon, Spivak, McClelland, Maier & Neustadt, L.L.P.

(57) ABSTRACT

A reaction unit containing a bottom part and a top part for pipetting a liquid, wherein the bottom part contains a reaction cavity with a permeable filter grid insert and the top part contains a reaction cavity which can be fixed on said bottom part and contains a cavity or covering for receiving a magnet.

32 Claims, 4 Drawing Sheets

(56) References Cited

U.S. PATENT DOCUMENTS

| | | | |
|---|---|---|---|
| 5,234,809 A * | 8/1993 | Boom et al. | 435/91.2 |
| 5,368,690 A * | 11/1994 | Solarek et al. | 162/175 |
| 5,645,723 A * | 7/1997 | Fujishiro et al. | 210/321.75 |
| 5,695,984 A * | 12/1997 | Argoudelis et al. | 435/253.5 |
| 5,702,631 A * | 12/1997 | Conville et al. | 252/76 |
| 5,746,978 A * | 5/1998 | Bienhaus et al. | 422/68.1 |
| 5,824,224 A * | 10/1998 | Fujishiro et al. | 210/651 |
| 5,895,631 A * | 4/1999 | Tajima | 422/513 |
| 5,985,153 A * | 11/1999 | Dolan et al. | 210/695 |
| 6,017,698 A * | 1/2000 | Bienhaus et al. | 435/6.19 |
| 6,074,827 A * | 6/2000 | Nelson et al. | 435/6.12 |
| 6,117,346 A * | 9/2000 | Kawaguchi et al. | 216/24 |
| 6,207,445 B1 * | 3/2001 | Crosby | 435/283.1 |
| 6,291,249 B1 * | 9/2001 | Mahant et al. | 436/177 |
| 6,455,325 B1 * | 9/2002 | Tajima | 436/526 |
| 6,576,460 B1 * | 6/2003 | Baeumner et al. | 435/287.1 |
| 6,607,662 B1 * | 8/2003 | Ikeda et al. | 210/175 |
| 6,713,271 B1 * | 3/2004 | Feistel | 435/7.92 |
| 6,723,237 B1 * | 4/2004 | Tajima | 210/222 |
| 6,770,246 B1 * | 8/2004 | Husek | 422/101 |
| 6,893,612 B2 * | 5/2005 | Kacian et al. | 422/570 |
| 6,919,175 B1 * | 7/2005 | Bienhaus et al. | 435/6.11 |
| 7,482,169 B2 * | 1/2009 | Gjerde et al. | 436/178 |
| 7,488,603 B2 * | 2/2009 | Gjerde et al. | 436/177 |
| 2006/0210435 A1 * | 9/2006 | Alavie et al. | 422/65 |

FOREIGN PATENT DOCUMENTS

| | | |
|---|---|---|
| WO | WO 96/41810 | 12/1996 |
| WO | WO 2005/065831 | 7/2005 |

* cited by examiner

FIG. 1

DEVICE AND PROCEDURE FOR AUTOMATED ISOLATION AND PURIFICATION OF NUCLEIC ACIDS FROM COMPLEX STARTING MATERIALS OF THE USERS CHOICE

BACKGROUND OF THE INVENTION

1. Field of the Invention

The subject of the invention is a device and a procedure for isolating nucleic acids from the most different of starting materials containing nucleic acids, which both guarantees a very high quality of the isolated nucleic acids as well as allowing the isolation of quantitative yields.

2. Description of the Background Art

Under classical conditions the isolation of DNA from cells and tissues is carried out such that the starting materials containing the nucleic acids are digested under highly denaturing and reducing conditions, with in part the use of protein-degrading enzymes, the released nucleic acid fraction is purified in phenol/chloroform extraction stages and the nucleic acids are isolated by dialysis or ethanol precipitation from the aqueous phase (Sambrook, J., Fritsch, E. F. und Maniatis, T., 1989, CSH, "Molecular Cloning").

These "classical procedures" for the isolation of nucleic acids from cells and especially from tissues are very time-consuming (in part longer than 48 h), require considerable apparative expenditure and moreover are not implementable under field conditions. In addition, such methods are hazardous to health, owing to the chemicals used in amounts that are not inconsiderable, such as phenol and chloroform.

Different alternative procedures for the isolation of nucleic acids from different biological starting materials allow the elaborate and health-damaging phenol/chloroform extraction of nucleic acids to be circumvented and a reduction in time expenditure to be achieved.

All of these procedures are based on a method for the preparative and analytical purification of DNA fragments from agarose gels developed and described for the first time by Vogelstein and Gillespie (Proc. Natl. Acad. Sci. USA, 1979, 76, 615 619). The method combines the dissociation in a saturated solution of a chaotropic salt (NaI) of the agarose containing the bands of the DNA to be isolated with binding of the DNA to glass particles. The DNA fixed to the glass particles is then washed with a wash solution (20 mM Tris HCl [pH 7.2]; 200 mM NaCl; 2 mM EDTA; 50% v/v ethanol) and then separated from the support particles.

Until now, this method has undergone a series of modifications and is currently used in different procedures for the extraction and purification of nucleic acids from different sources (Marko, M. A., Chipperfield, R. und Bimboim, H. G., 1982, Anal. Biochem., 121, 382 387).

In addition, a plurality of reagent systems exists worldwide today, predominantly for the purification of DNA fragments from agarose gels and for the isolation of plasmid DNA from bacterial lysates, and also for the isolation of longer-chain nucleic acids (genomic DNA, cellular total RNA) from blood, tissues or cell cultures.

All these commercially available kits are based on the well-known principle of binding nucleic acids to mineral supports in the presence of solutions of different chaotropic salts, and use suspensions of finely-milled glass powder (e.g. Glasmilk, BIO 101, La Jolla, Calif.), diatomaceous earths (Sigma) or silica gels as support materials (Diagen, DE 41 39 664 A1).

A procedure for the isolation of nucleic acids which is practicable for a number of different applications is proposed in U.S. Pat. No. 5,234,809 (Boom). A procedure is described therein for the isolation of nucleic acids from starting materials containing nucleic acids, whereby the starting material is incubated with a chaotropic buffer and a DNA-binding solid phase. The chaotropic buffer carries out both the lysis of the starting material as well as the binding of the nucleic acids to the solid phase. The procedure is well suited for the isolation of nucleic acids from small amounts of sample, and finds practical use particularly in the area of the isolation of viral nucleic acids.

Specific modifications of these procedures concern the use of novel support materials which have applicative advantages for particular problems (WO-A 95/34569).

More recent patent applications disclose that so-called antichaotropic salts can be used very efficiently and successfully as components of lysis/binding buffer systems for the adsorption of nucleic acids to silicate materials known and used by the person skilled in the art (EP 1135479).

Also part of the background art is the U.S. Pat. No. 6,207, 445 B1, in which a simple to use filtration and extraction device for a biological fluid is described, which makes a sample directly available to an analytic procedure. The device is capable of making a purged fluid directly available for analysis or for disposal, for which it is suited to the specific analyte of note. And it is capable of capturing particle-shaped materials and allows for a further treatment, i.e. an extraction of these particles directly with the device. As soon as it has been extracted once, the device makes a fluid containing the analyte of note available to an analytic procedure. The device comprises a bendable body with an open upper and an inner wall which defines an inner chamber. A closing, or rather sealing, mechanism is set up in such a way to seal off the open upper end of the body. A graded filter apparatus containing at least one filter is incorporated into the body by a support apparatus. The elastic body is set up in such a way that, when pushed together by a user's finger, a positive pressure is generated in the chamber, which is enough to cause a fluid to flow into the chamber through the filter apparatus.

In U.S. Pat. No. 6,207,463, a device for separating magnetic particles from a stock composition is described. This device contains a longitudinally-stretched protective covering with an upper and a lower end, an inner space enclosed by the protective covering, which protrudes from its upper end to its lower end, an adjustable bar magnet which is arranged in the inner space, lengthwise to it.

A device for separating and cleaning a suspension with magnetic particles is described in the published international patent application WO2005/063831 A1. This device comprises a process area with mechanisms moving synchronously for the transport of magnetic microparticles in the x direction.

The analysis of the state of the art illustrates quite impressively that a plurality of possibilities exists to bind nucleic acids to solid support materials, in particular silicon-based mineral support materials, then to wash and to release once more the nucleic acids from the support material.

On the basis of the technologies described for the binding of nucleic acids onto solid support materials, there exists a plurality of commercially-available products which enable users to isolate nucleic acids from starting materials containing nucleic acids. Procedural solutions which are thereby increasingly interesting are those which permit nucleic acids to be automatically isolated and purified. This is accounted for by their reducing the considerable manual effort, or being able to implement high capacities of nucleic acid extraction. Taking account of these requirements, there are robot- or machine-based solutions for the isolation of nucleic acids. As a rule, this makes for very complex device configurations, which make the isolation of nucleic acids possible. In general, one can distinguish between two system configurations.

1. Automated procedures for the isolation of nucleic acids by the use of 96 Well filter plates to bind the nucleic acids.
2. Automated procedures for the isolation of nucleic acids by the use of magnetic particles to bind the nucleic acids.

The process of isolation of the nucleic acids is thereby implemented analogously to the manual procedure described. After lysis of the starting material takes place the binding of the nucleic acids to the particular solid support materials (filter plates or magnetic particles), and then the growing of the bound nucleic acids, drying of the support materials (removal of alcoholic components) and elution of the nucleic acids. The processing of the extraction in the case of use of filter plates is thereby carried out via vacuum or by means of pressure, or rather upon use of magnetic particles over a magnetic separation.

The task of the robot stations is, if possible, to automatically reproduce all the necessary procedural steps of a nucleic acid extraction. This is accomplished by complex pipetting steps by means of dispensation devices which must have the different buffer components to hand, vacuum stations for the filtration, or rather magnetic separators for use of magnetic particles, integration of complex centrifugal technology if appropriate. Heating units and shaking units are also preferably used to support the lysis processes.

However, there are only very few highly-specialized machines which enable the user to carry out the whole process of isolation of nucleic acids. In addition, these devices are often in no way universally applicable, but rather are only optimized for highly specialized application solutions. A further extreme disadvantage is the extremely high cost for the acquirement of such a machine. This is further exacerbated by what can be an extremely high rate of use of expendable materials, in particular pipette tips for the pipetting steps. Hence sometimes several hundred pipette tips can be required for certain uses for the isolation of nucleic acids by means of 96 Well filter plates.

Cost-effective systems are e.g. device solution which enable the user to isolate nucleic acids partially automatically by means of magnetic particles (e.g. KingFisher (trade name)). These devices have been specially developed for the isolation of nucleic acids and work according to a simple "walk-away" principle. The samples to be treated, as well as necessary buffer solutions for the binding, washing and elution steps, are carried over in reaction activities, such that the separation of the magnetic particles takes place over bar magnets which initiate the process of nucleic acid isolation by the contacting of the magnetic particles with the different buffer solutions. A new procedure is disclosed in EP1382675. Here, the process of isolation of nucleic acids is carried out by the use of a novel and extremely thin membrane. This membrane is a constituent of a filter cartridge. This filtration unit is a core part of an extraction device which carries out partial processes of the isolation of nucleic acids (binding, washing, elution) automatically. In this, a pre-lysed sample is introduced into the filtration unit by the user. The progress of the sample across the filter membrane can be carried out by vacuum. Subsequent wash solutions are automatically suspended and sucked across the membrane. The elution step takes place after addition of an elution buffer in the same form.

These latter device systems are much more cost-effective than the extraction robots already described.

But what is disadvantageous about these systems is the extremely small degree of automation. These systems only automate partial steps of procedures for the isolation of nucleic acids. The total progress of the sample pre-treatment, and in particular the sample lysis, is not carried out by means of these devices. The automated extraction is only carried out after lysis of the sample. In addition, the lysed sample is not once taken on automatically by the device, but rather must be manually introduced. The KingFisher system moreover requires time-consuming and labor-intensive steps in order to fill all buffer components into the reaction plastic intended for them.

The very low degree of automation therefore places a great limitation on the field of application of this device.

A further substantial problem in connection with an automation of procedures for the isolation and purification of nucleic acids, particularly those of complex starting materials (textiles, mousetail, plants, foodstuffs, stool samples etc.), consists in the separation of undissolved starting materials after lysis has been carried out. As a rule, up to now this could only be achieved by a centrifugation step for the pelleting of the undissolved components (further treatment with the supernatants), or rather by means of a centrifugation over a filter (further treatment with the filtrates). As the integration of such procedural steps is hardly possible with the established machines, automated purification of samples which are in this way problematic is impossible or only insufficiently achieved.

BRIEF DESCRIPTION OF DRAWINGS

FIG. 1 shows the construction of a reaction unit according to the invention.

DETAILED DESCRIPTION OF THE INVENTION

Figure 2:
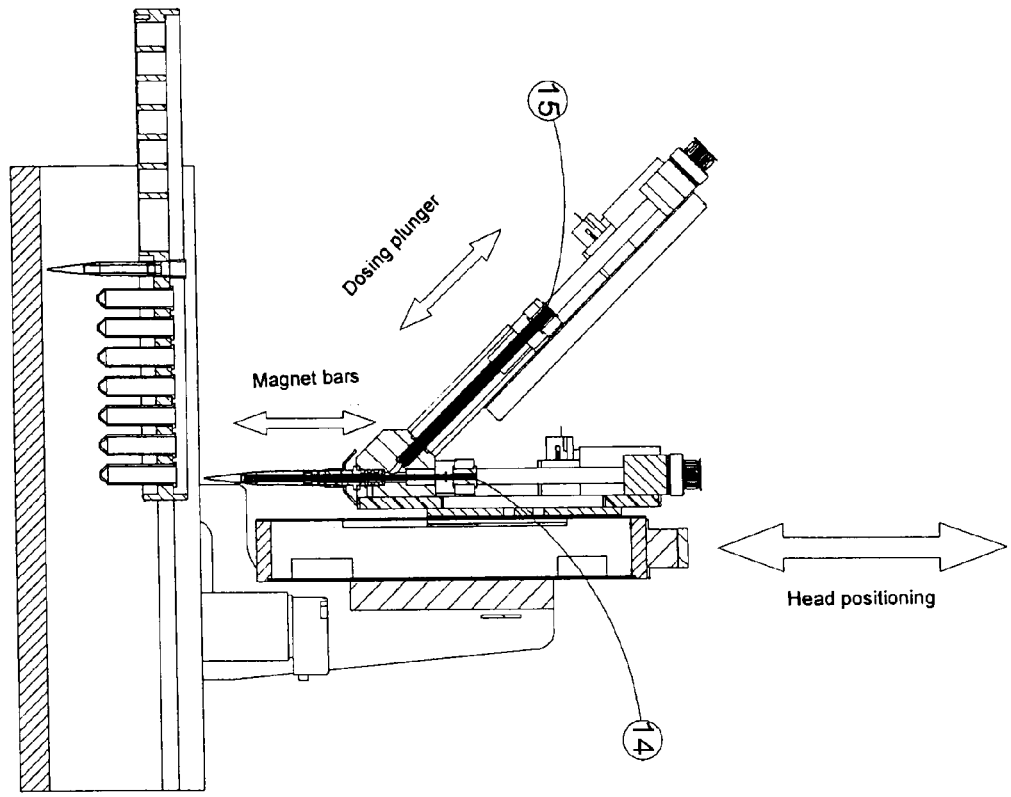
FIG. 2 shows an extraction machine.
Figure 2:
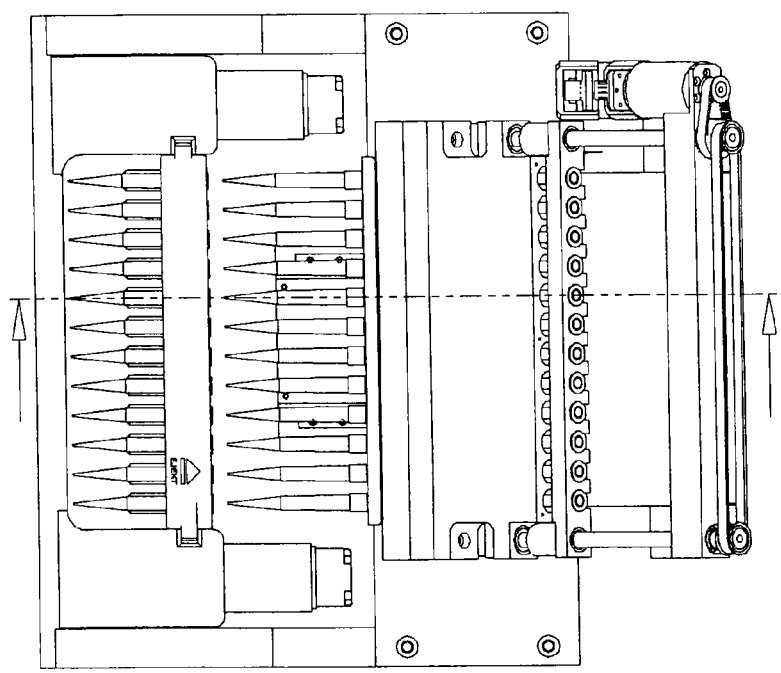

It is an object of the present invention to overcome the disadvantages of the background art.

This and other objects have been achieved by the present invention the first embodiment of which includes a reaction unit, comprising:
a bottom part and a top part for pipetting a liquid,
wherein the bottom part comprises a reaction cavity with a permeable filter grid insert and the top part comprises a reaction cavity which can be fixed on said bottom part and contains a cavity or covering for receiving a magnet.

The present invention also relates to an apparatus, comprising:
at least one reaction unit as above.

The present invention further relates to a method for the isolation and purification of a nucleic acid from a complex starting material, comprising:
lysis of the starting material,
binding of the nucleic acid to magnetic particles, to obtain a bound nucleic acid and, optionally, filtration of undissolved components,
washing and drying of the bound nucleic acid, and
elution of the bound nucleic acid, to obtain said nucleic acid.

The present invention further provides a method for the selective simultaneous isolation of genomic DNA from cellular RNA from a complex starting material, comprising:
lysis of the starting material,
isolation of the genomic DNA, and
isolation of the RNA.

The processes for isolation of nucleic acids are implemented in a highly automated fashion, the quantities of required expendable materials are kept low, flexible sample sizes are treated and the process of isolation of the nucleic acids is accelerated.

By this, nucleic acids are isolated automatically and without additional manual intervention from difficult, complex samples, in particular with regard to the presence of solid, undissolved components. What is more, first of all both genomic DNA and also cellular total RNA are isolated from a sample simultaneously and in parallel.

The procedure according to the invention and the devices according to the invention fulfill objects posed for the present in the most ideal fashion.

Figure 1:
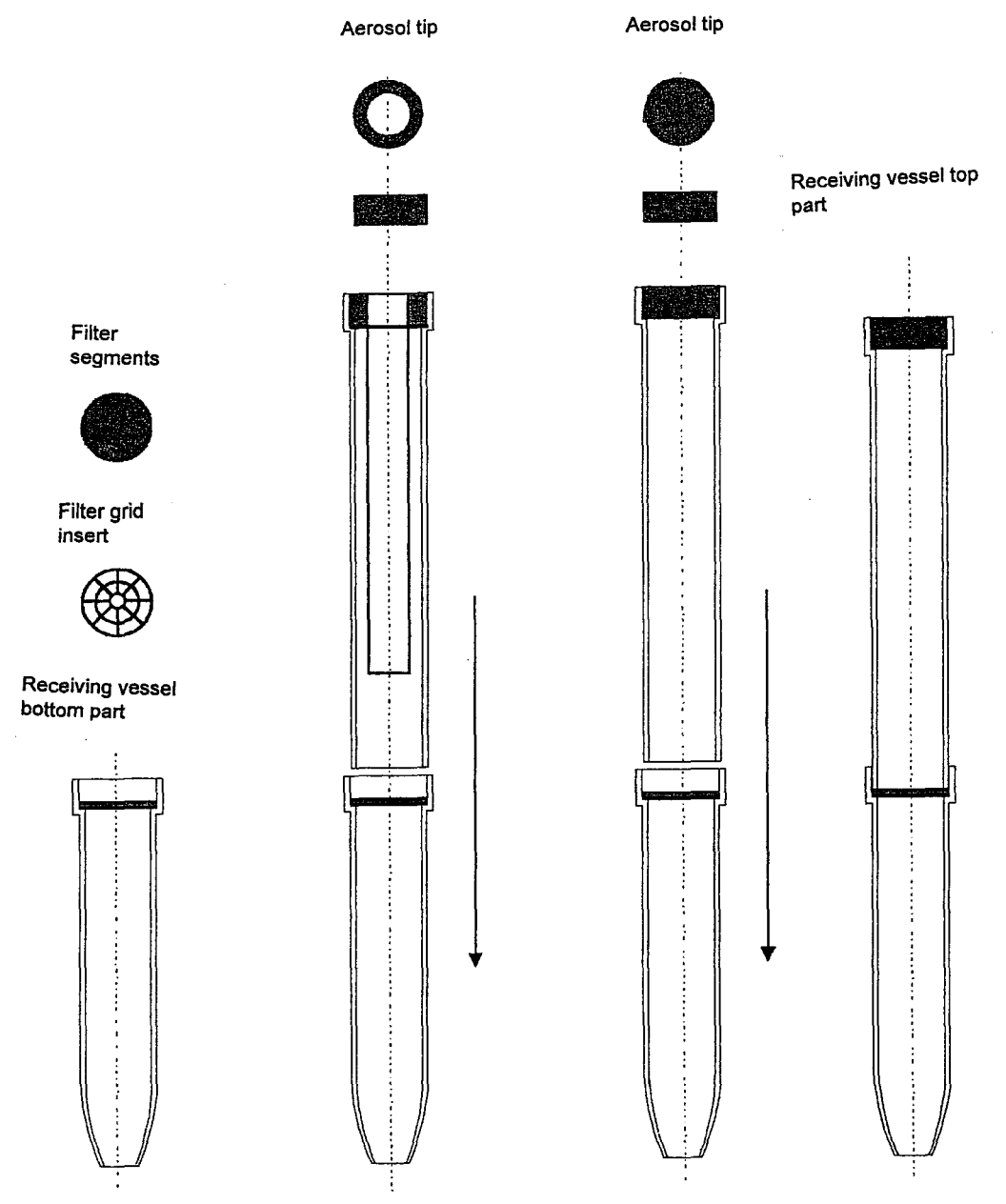

A core piece of the reaction process is therefore a reaction unit composed of a top and a bottom part. The bottom part of the reaction unit thereby consists of a reactive activity with a permeable filter grate insert. In the process of the invention, this filter grate insert serves in the separation of particular components after lysis of a complex biological sample. Moreover, this insert optionally also serves as a contact surface for a solid support material for the binding of biomolecules to be isolated (e.g. a fiberglass web or a membrane). These variants are, then, particularly used if the genomic DNA and the cellular total RNA have to be simultaneously isolated from a biological sample. The top part of the reaction unit consists of a reaction cavity into which a plastic covering is brought. In addition, the top part contains a filter material to protect against aerosols. The finished reaction unit comes about by the combination of top part and bottom part. If a chromatographic filter material is used, then this is also fixed in place on the filter unit by contacting of top and bottom parts. The top part of the reaction unit thereby fixes the filter material. After combination of top and bottom part, the reaction unit is functionally active. FIG. 1 shows the construction of a reaction unit according to the invention. The instrument according to the invention has a multiplex function for the process of nucleic acid isolation to be carried out.

According to the invention, the instrument serves in:

1. an exact dispensation and pipetting of liquids,
2. a separation of solid and undissolved components after lysis of the sample to be treated,
3. the isolation of nucleic acids by use of magnetic particles,
4. the isolation of nucleic acids by their chromatographic binding to a solid support material (as an optional constituent of the reaction unit).

The reaction unit is thereby a core piece of a machine. It consists of positions for receiving trade standard reaction vessels as well as reservoir vessels for liquids as well as an insertion position for the reaction units according to the invention. A reaction vessel position can optionally be heated.

The extraction machine further contains a suction or compressed air device. This unit is coupled with a dispensing head which is exactly adapted to the reaction units. The compressed air unit is coupled to a heat source which makes is possible to dispense heated air as well. In the dispensing head there is moreover a kinematic unit for the vertical movement of magnetic pins. Further, the extraction machine contains an interface for communication with a computer which controls all the program sequences.

A process according to the invention for isolating nucleic acids, e.g. genomic DNA from a biological sample, is carried out as follows by means of the procedure according to the invention. In general, the treatment of a sample for the isolation and purification of nucleic acids is carried out according to the sequence lysis—binding—washing—elution. The process can thereby be carried out completely automatically. All buffer components necessary for the extraction are found on the machines in the reservoir vessels or in the reaction vessels. At the beginning of the extraction, the sample to be treated is transferred into reaction vessels and placed on the machines. The procedure for isolating the nucleic acid divides into the processes of filling the reaction vessels, lysis of the initial sample and extraction of the nucleic acids (via binding of the nucleic acids to magnetic particles, washing the bound nucleic acids, drying of the magnetic particles and elution of the nucleic acids). The whole process according to the invention is thereby always carried out with one reaction unit per sample to be treated. This serves in the multiplex function according to the invention for dispensing/pipetting, or rather filtration and extraction of the nucleic acid.

The reaction unit of the present invention and extraction apparatus of the present invention which contains at least one reaction unit are used for a) an exact dispensation and pipetting of liquids and/or
b) a separation of solid, undissolved components after lysis of a sample to be treated and/or
c) the isolation of nucleic acids by use of magnetic particles and/or
d) the isolation of nucleic acids by their chronometric binding and a solid support material.

Having generally described this invention, a further understanding can be obtained by reference to certain specific examples which are provided herein for purposes of illustration only, and are not intended to be limiting unless otherwise specified.

Exemplary Embodiments

Exemplary Embodiment 1

The extraction process for the isolation of e.g. genomic DNA proceeds as follows:

A. Process for Filling the Reaction Vessels

1. Reception of the reaction units by the dispensing head.
2. Filling of the reaction vessels with the buffers from the reservoir vessels.

The reaction unit thereby acts as a classic pipetting device (suck up buffer and dispense buffer). The filling is carried out according to a predetermined schema in the manner that the basis is always the solution with the lowest concentration of salt, so that for the filling of the reaction vessel treatment is also only carried out with one reaction unit. Filling is done in the following sequence: Eluent—washing buffer—lysis buffer.

These buffer components are all found in the reservoir vessels on the machine platform.

3. Transfer of the sample into the reaction vessel with the lysis buffer provided.

B. Lysis Process of the Starting Material

1. The lysis of the sample is carried out (by associated tempering, if necessary) by repeated continual pipetting in and out of the lysis additive by means of the reaction unit.
2. After lysis the reception of the binding buffer and magnetic particle by means of the reaction unity is carried out, as is transfer of the binding buffer and the magnetic particles into the lysis additive. The binding buffer with the magnetic particles is not located in reservoir vessels, in contrast to the other buffer components, but rather in separate reaction vessels.

C. Nucleic Acid Extraction/Possible Filtration of Undissolved Components

1. Mixing of the lysis/binding buffer additive and the magnetic particles with the reaction unit (by pipetting in and out).
2. Binding of the nucleic acid to the magnetic particles and subsequent filtration of undissolved substances as well as magnetic separation. This is carried out by absorption of the sample from the bottom part of the reaction unit, over the filter grid, into the top part of the reaction unit. By this process, the lysed sample (including the magnetic particles) is transported over the filter grid. The lysed sample with the magnetic particles contained therein is now located in the top part of the reaction unit. The magnetic separation is carried out subsequently by the introduction of a magnetic pin from the dispensing head into the plastic covering of the top part of the reaction unit. In this process, the magnetic particles are drawn through the magnetic pin onto the plastic covering, and remain in this position. The undissolved components possibly present are located in the bottom part of the reaction unit. After binding of the magnetic particles to the plastic covering, the sample is subsequently given back into the initial reaction vessel from the top part of the reaction unit. The magnetic particles with the bound nucleic acid remain on the plastic covering.

3. Washing of the nucleic acid bound to the magnetic particles. Thereby, transferral of the dispensation unit with reaction unit to the next row of reaction vessels (with washing buffers contained therein). This transfer can be carried out either by an incremental movement of the dispensing head, or by incremental movement of the reaction vessels. In the latter case the dispensing head is immobile. After a successful kinematic step, the reaction unit is located over the reaction vessel with washing buffer contained therein. Subsequently, the reaction unit dips into the reaction vessel with washing buffer, and the washing buffer is sucked in up to the top part of the reaction unit. Washing of the magnetic particles is carried out by outward movement of the magnetic pin. The magnetic particles are thereby released by the plastic covering and efficiently mixed in the washing buffer (washed) by alternating (repeated, if necessary) absorption and ejection of the washing buffer from the bottom part of the reaction unit over the filter into the top part of the reaction unit. The washing step is ended in that, after final suction of the washing buffer into the top part of the reaction unit, the magnetic pin subsequently moves from the dispensing head into the plastic covering of the top part of the reaction unit, the magnetic particles are drawn through the magnetic pin onto the plastic covering and there remain in this position. Finally, the washing buffer is given back into the reaction vessel. The washing steps can be repeated many times by the described relative movement of the reaction vessel with the buffer contained therein, or by movement of the dispensing head.

4. Drying the filter. To this end, the reaction unit is located over an empty reaction vessel. The drying is carried out by application of compressed air (heated, if necessary) and through-flow of the air over the magnetic particles magnetically fixed to the plastic covering.

5. Elution of the bound nucleic acid. For this, transfer of the dispensing unit with reaction to the next row of reaction vessels (with elution buffers contained therein), or rather transfer of the next row of reaction vessels to the immobile dispensing head. In turn, immerse reaction unit in reaction vessel with elution buffer, and suck up elution buffer into the upper part of the reaction unit.

The elution of the nucleic acid by the magnetic particles is carried out by deployment of the magnetic pin. The magnetic particles are thereby released by the plastic covering and efficiently mixed in the washing buffer (washed) by alternating (repeated, if necessary) suction and ejection of the washing buffer from the bottom part of the reaction unit over the filter into the top part of the reaction unit. The elution step is ended in that, after final absorption of the washing buffer into the top part of the reaction unit, the magnetic pin subsequently moves from the dispensing head into the plastic covering of the top part of the reaction unit, the magnetic particles are drawn through the magnetic pin on to the plastic covering and there remain in this position. Finally, the elution buffer (the isolated nucleic acid) is given back into the reaction vessel.

The isolated nucleic acid is now present in the last reaction vessel, and can be introduced for the planned "downstream" use.

As depicted, the instrument and procedure according to the invention make the isolation of nucleic acids possible in a quite simple way by means of the sequences of suction and dispensation of liquids in combination with the use of magnetic particles. The "walk-away concept" makes the process of extraction extremely fast, as pipetting steps necessary up to now are completely done away with. The multiple functions of the reaction unit according to the invention enable the complete filling of all necessary reaction vessels, if necessary the filtering off of undissolved constituents after sample lysis, as well as the isolation of nucleic acids by their binding to magnetic particles. The large use of plastic materials, conventional until now, reduces down to only one reaction unit/sample. The integration of lysis processes, including if necessary the removal of unlysed sample components, in the automated extraction sequence represents a decisive advantage compared with the alternative and commercially-available extraction devices described. What is more, the machine according to the invention can be introduced by the choice of the dispensing head for different sample capacities. For this reason, the instrument according to the invention is not established in specific formats and can be flexibly adapted to the requirements of the user. This measure of flexibility in relation to the sample quantities to be treated makes it possible to use the machines efficiently even with small preparation quantities, and thereby to fully exploit the advantage of the automation of the process.

The process of isolation of the nucleic acids is achieved in an extremely short time. After successful lysis of the initial sample, the process of nucleic acid extraction is entirely completed in a few minutes, as all necessary process are executed extremely quickly due to the "walk-away concept" (e.g. after lysis, no more liquid handling steps are necessary). The extremely fast process execution, in combination with the possibility of a different assembly of the machines with various dispensing heads for the reception of a different-sized quantity of reaction units, makes it possible to treat even large sample amounts extremely quickly and efficiently in a fully automated extraction process. What is more, only very few so-called "consumables" are required.

A further advantage of the instrument according to the invention concerns the process of nucleic acid extraction. The isolation of the nucleic acids is carried out, as has already been described, by the binding of the nucleic acids to magnetic particles. In this way, the instrument according to the invention is compatible to all the procedural solutions known to the person skilled in the art for the isolation of nucleic acids. This concerns both the potential use of different magnetic particles hitherto unknown (combination of chemistry and surface functionalization of the magnetic particles) and the potential use of the most different buffer formulations, which make an isolation of nucleic acids possible. These possibilities underline the enormously broad potential spectrum of use of the instrument according to the invention.

The highly integrative complexity of the instrument according to the invention makes it finally possible to isolate nucleic acids from the most different starting materials highly efficiently, without limitations with regard to the extraction chemistry.

The procedural sequences described were, until now, always related only to the isolation of nucleic acids from a sample. This means that both DNA and RNA can be isolated, or rather that by the choice of suitable buffer combinations for the binding of nucleic acids to the magnetic particles, the isolation of DNA and RNA can also take place at the same time.

The separate isolation of DNA and RNA from a biological sample is, however, very challenging. This is of great importance for a raft of applications.

The aim of the present invention also consisted in isolating automated DNA and RNA from a sample. This is achieved by use of the reaction units according to the invention, as follows. As has already been depicted, the reaction unit is also introduced for the chromatographic isolation of nucleic acids. To this end, a chromatographic filter material known to those skilled in the art (e.g. fiberglass web) is brought onto the filter insert of the reaction unit and fixed by means of the top part of the reaction unit. The procedure of simultaneous and separated isolation of DNA and RNA from a sample is based on the following mechanism. The chromatographic material (fiberglass web) fixed in the reaction unit serves in the selective binding of genomic DNA, the magnetic particles coming into use, on the other hand, in the binding of the RNA to be isolated. The combination of a filter material with magnetic particles for selective and separate isolation of DNA and RNA have not yet been described.

The generally preparatory steps of loading the reaction vessel on the machine platform are carried out, as has already been described, by means of the reaction unit according to the invention and its pipetting functions. If all necessary pipetting solutions are provided, then the process of separate and parallel isolation of DNA and RNA follows on like this:

Exemplary Embodiment 2

A. Selective Isolation of the Genomic DNA from a Sample by the Binding of the Filter Material Introduced.

1. Lysis of the Starting Material

The lysis of the sample is carried out by means of lysis buffers known to those skilled in the art on the basis of strongly denatured chaotropic salts as well as further additives like DRR and detergents (if necessary by attached tempering) through multiple continuing pipetting in and out by means of the lysis additive by means of the reaction unit. A reaction unit according to the invention is used which contains a fiberglass web on the filter cartridge.

2. Isolation of the Genomic DNA

Binding of the genomic DNA to the filter material of the reaction unit. This is carried out by alternately absorbing and ejecting the sample from the bottom part of the reaction unit, over the filter, into the top part of the reaction unit. By this sequence, the lysed sample is transported over the filter. In this sequence, the DNA contained in the sample binds selectively to the filter material, but the RNA does not. The sequence of the sample passage over the filter can be carried out many times. This can be achieved in that the binding conditions of the lysis buffer are not suited to the binding of RNA, but are highly efficient for the binding of genomic DNA Finally, the lysate is given back into the reaction vessel with the RNA which is now still just contained.

3. Washing of the DNA bound to the filter. Thereby, transferral of the dispensation unit with reaction unit to the next row of reaction vessels (with washing buffers contained therein). Immerse reaction units in turn in reaction vessels with washing buffers, and pass washing buffers from the bottom part of the reaction unit over the filter into the top part of the reaction unit by alternate (multiple, if necessary) absorption and ejection of the washing buffer. Repeat step in a further reaction vessel with washing buffer. Finally, the washing buffer is given back into the reaction vessel.

4. Drying the filter. To this end, the reaction unit is located over an empty reaction vessel. The drying is carried out by application of compressed air (heated, if necessary) and flow of the air over the filter.

5. Elution of the bound DNA. To this end, transfer of the dispensation unit with reaction unit to the next row of reaction vessels (with elution buffers contained therein). Immerse reaction units in turn in reaction vessels with elution buffers, and pass elution buffers from the bottom part of the reaction unit over the filter into the top part of the reaction unit by alternate (multiple, if necessary) absorption and ejection.

The isolated DNA is now present, purified, and can be introduced for the planned "downstream" use.

1. Subsequent Isolation of the Total RNA by Binding to Magnetic Particles.

As has already been depicted, the RNA to be isolated is located in the initial sample in the lysis additive (after removal of the DNA). The reaction unit is warped with the fiberglass mesh contained therein in preparation. The machine takes on a second reaction unit. This, however, contains no fiberglass. The process of isolation of RNA is carried out by binding onto the magnetic particles as is described in what follows.

2. Setting optimal binding conditions for RNA. Addition of an alcoholic binding buffer and of the magnetic particles into the remaining lysis additive. The pipetting takes place, as has already been described, with the reaction unit according to the invention. Mixing of the lysis/binding buffer additive and the magnetic particles with the reaction unit (by pipetting in and out).

3. Binding of the RNA to the magnetic particles. This is carried out by absorption of the sample from the bottom part of the reaction unit into the top part of the reaction unit. The lysed sample with the magnetic particles contained therein is now located in the top part of the reaction unit. The magnetic separation is carried out subsequently by the introduction of a magnetic pin from the dispensing head into the plastic covering of the top part of the reaction unit. In this process, the magnetic particles are drawn through the magnetic pin onto the plastic covering, and remain in this position. After binding of the magnetic particles to the plastic covering, the sample is subsequently given back into the initial reaction vessel from the top part of the reaction unit. The magnetic particles with the bound nucleic acid remain on the plastic covering.

4. Washing of the RNA bound to the magnetic particles. Thereby, transfer of the dispensation unit with reaction unit to the next row of reaction vessels (with washing buffers contained therein). This transfer can be carried out both by an incremental movement of the dispensing head, or by incremental movement of the reaction vessels. In the latter case the dispensing head is immobile. After a successful kinematic step, the reaction unit is located over the reaction vessel with washing buffer contained therein. Subsequently, the reaction unit dips into the reaction vessel with washing buffer, and the washing buffer is sucked in up to the top part of the reaction unit. Washing of the magnetic particles is carried out by outward movement of the magnetic pin. The magnetic particles are thereby released by the plastic covering and efficiently mixed in the washing buffer (washed) by alternating (repeated, if necessary) absorption and ejection of the washing buffer from the bottom part of the reaction unit into the top part of the reaction unit. The washing step is ended in that, after final suction of the washing buffer into the top part of the reaction unit, the magnetic pin subsequently moves from the dispensing head into the plastic covering of the top part of the reaction unit, the magnetic particles are drawn through the magnetic pin on to the plastic covering and there remain in this position. Finally, the washing buffer is given back into the reaction vessel. The washing steps can be repeated many times by the described relative movement of the reaction vessel with the buffer contained therein, or by movement of the dispensing head.

5. Drying the filter. To this end, the reaction unit is located over an empty reaction vessel. The drying is carried out by application of compressed air (heated, if necessary) and through-flow of the air over the magnetic particles fixed to the plastic covering.

6. Elution of the bound RNA. For this, transfer of the dispensing unit with reaction unit to the next row of reaction vessels (with elution buffers contained therein), or rather transfer of the next row of reaction vessels to the immobile dispensing head. In turn, immerse reaction unit in reaction vessel with elution buffer, and suck up elution buffer into the upper part of the reaction unit.

The elution of the RNA by the magnetic particles is carried out by deployment of the magnetic pin. The magnetic particles are thereby released by the plastic covering and efficiently mixed in the washing buffer (washed) by alternating (repeated, if necessary) absorption and ejection of the washing buffer from the bottom part of the reaction unit over the filter into the top part of the reaction unit. The elution step is ended in that, after final absorption of the washing buffer into the top part of the reaction unit, the magnetic pin subsequently moves from the dispensing head into the plastic covering of the top part of the reaction unit, the magnetic particles are drawn through the magnetic pin onto the plastic covering and there remain in this position. Finally, the elution buffer (the isolated nucleic RNA) is given back into the reaction vessel.

The isolated RNA is now present in the last reaction vessel, and can be introduced for the planned "downstream" use.

As depicted, the instrument and procedure according to the invention make possible the simultaneous and parallel isolation of genomic DNA and RNA from an initial sample by means of the sequences of absorption and ejection of liquids in combination with the use of magnetic particles and chromatographic membranes known in themselves. A further advantage is founded in that fact that by selective isolation of the DNA, the isolated RNA is free of genomic DNA. Until now, this has always been a problem in extraction procedures for the isolation of cellular total RNA known in themselves.

The "walk-away concept" makes the process of simultaneous and parallel extraction of DNA and RNA extremely fast, as pipetting steps necessary up to now are completely done away with. The multiple functions of the reaction unit according to the invention make possible complete filling of all necessary reaction vessels as well as the isolation of the DNA and RNA out of an initial sample. The large use of plastic materials, conventional until now, reduces down to only two reaction units/samples. The integration of the lysis process into the automated extraction sequence represents a decisive advantage compared with the alternative and commercially available extraction devices described. Finally, by the combination according to the invention of two totally different solid phases, the combination of filter membranes and magnetic particles can be implemented in an extraction sequence, a highly efficient and, over the machines depicted, an extremely fast simultaneous and parallel isolation of DNA and RNA from the initial sample. Such a procedure is no longer available.

Exemplary Embodiment 3

Extraction Machine for Automated Isolation of Cellular Total RNA

The device is developed as a bench top device and consists of kinematics with four degrees of freedom, a 12-channel dosage head and a manually-loadable tray.

The following movements are achieved by the kinematics (reference numerals are for FIGS. 2 and 3, respectively):

Collection and positioning of the tray (11) in the Y axis.

Position of the dosing head in the Z direction for automatic acceptance of the tips (12), (13).

To lower the tips (13) into the tubes (1-5) and the reservoirs (6-10).

Positioning of the magnetic columns (14).

Positioning of the dosing pump (15).

Dosing Head Function:

The dosing head can take on 12 multifunction sprays (12), (13) automatically from the tray, pipette 21 solutions in parallel and position 12 magnetic columns for magnetic separation.

The Function of the Tray:

The tray is manually loaded outside of the device with multifunction sprays and filled with solutions. 12 filtrates are placed into the tray. (See A. Preparatory steps)

B. Automated Extraction Process

1. Addition of magnetic particles into the filtrate of step 6 and placing of the receiver tube in position 1 of the robot.

2. Automatic loading of the receiver tube on the robot with the following solutions:

Receiver Tube Position (5): RNA-free water from reservoir (9),

Receiver tube position (4): empty,

Receiver Tube Position (3): washing solution LS (800 µl) from reservoir (8), Receiver Tube Position (2): washing Solution HS (500 µl) from reservoir (7), Receiver Tube Position (1): binding Solution EG (500 µl) from reservoir (6).

3. Mixing the filtrate with the magnetic particles and the binding solution EG on position (1). Magnetic separation within the reaction unit. Movement of the reaction unit to receiver tube (2).

4. Washing of the particles in washing solution HS. Magnetic separation. Movement of the reaction unit to receiver tube (3).

5. Washing of the particles in washing solution LS. Magnetic separation. Movement of the reaction unit to receiver tube (4).

6. Drying of the particles (4).

Figure 3:
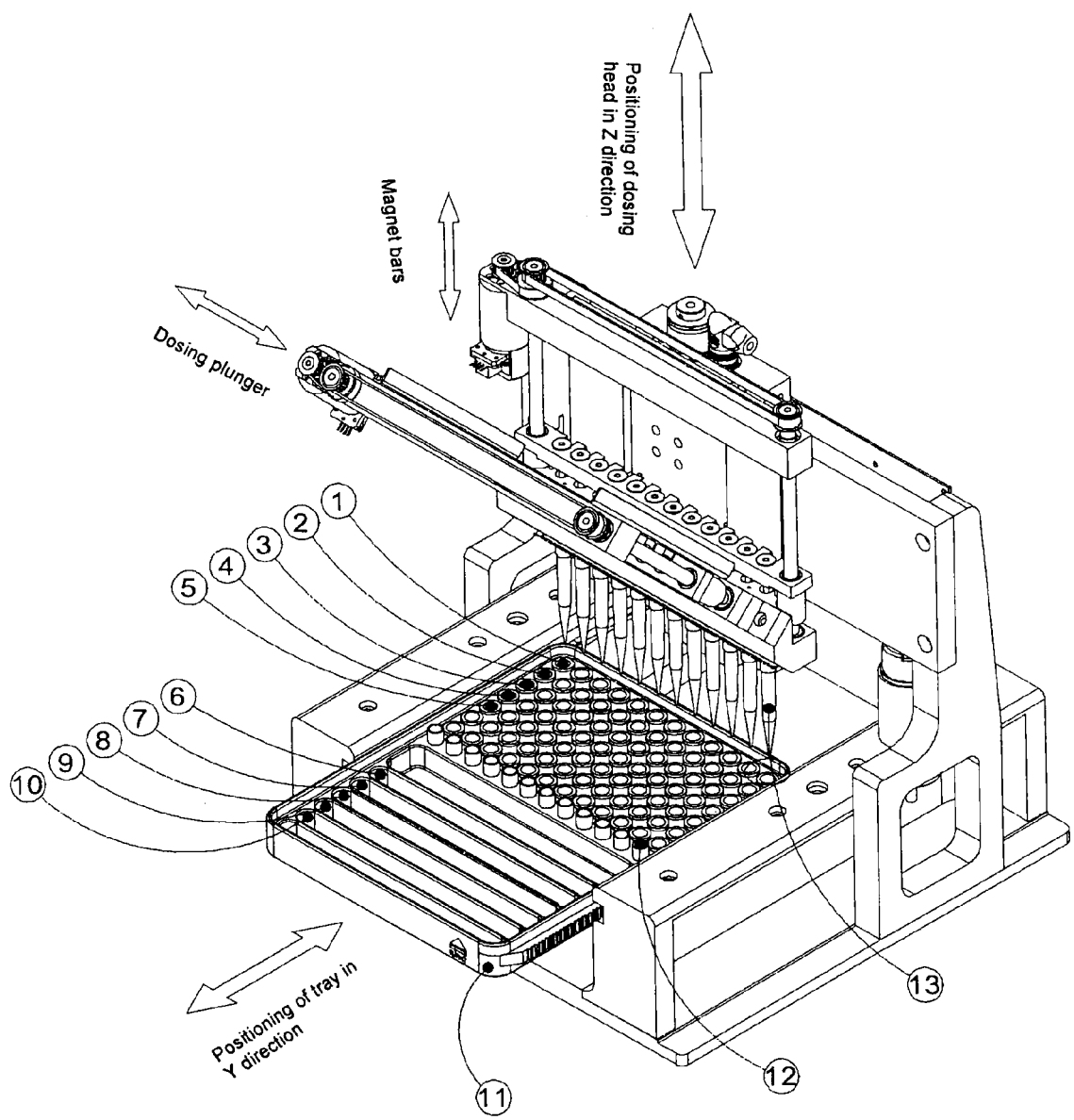
FIG. 3 shows an extraction machine.
Figure 4:
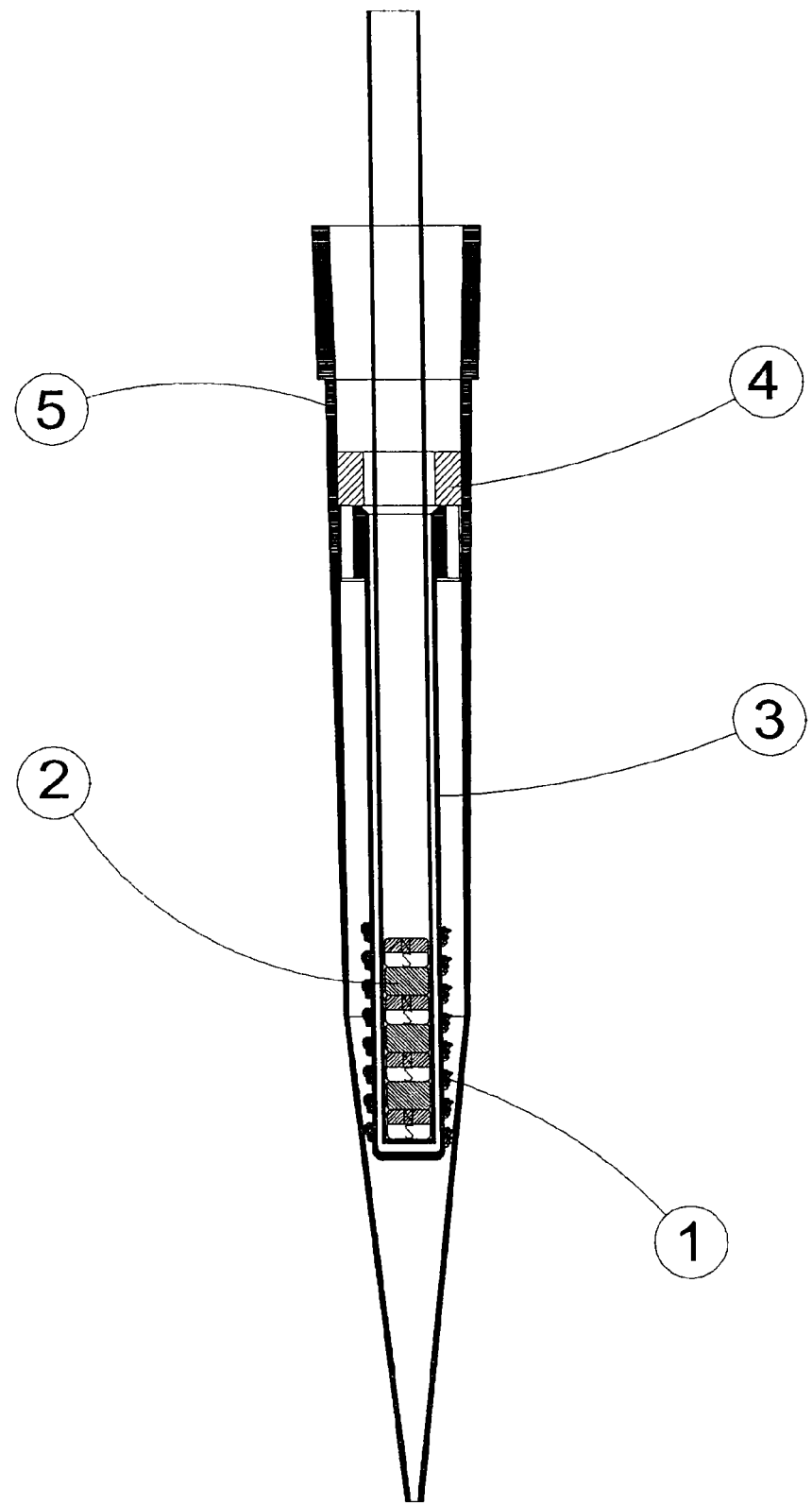
FIG. 4 shows an embodiment of a reaction unit of the present invention.

7. Movement of the reaction unit to receiver tube (5). Desorption of the RNA by the particles. Magnetic separation. RNA is located in the receiver tube in position (5) END of the extraction The reaction unit according to the invention is depicted in what follows under FIG. 1. The variant depicted should not thereby represent any restrictions to the instrument according to the invention. FIGS. 2 and 3 show the extraction machines. FIG. 4 shows a special variant of the reaction unit. The reference numerals in FIG. 4 are:

1 Magnetic particles,

2 Magnets with plastic parts,

3 Covering,

4 Septum, and

5 Top part of the reaction unit.

A permeable filter grate insert is not shown in FIG. 4. This special kind of device can be used if no undissolved constituents have to be separated off. The septum prevents any liquids from being absorbed too far upwards.

German patent application DE 10 2005 053 463.5 filed Nov. 6, 2005 and international application PCT/EP2006/068147, filed Nov. 6, 2006, are incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A reaction unit for a machine which separates nucleic acids, comprising:
    a bottom part which inserts into an insertion position of the machine; and
    a removable top part which is combined with a bottom part; wherein
    the bottom part comprises:
    an end for insertion into the machine; and
    an end which combines with the top part; wherein
    the insertion end has an opening at the insertion position for the passage of liquids to and from the machine; and
    a reaction cavity having a permeable filter grid insert at the end which combines with the top part, and wherein
    the top part comprises:
    a reaction cavity which combines with a bottom part; and a space or covering for receiving a magnet; and a magnet insertable into the reaction cavity to effect movement of magnetic particles.

2. The reaction unit according to claim 1, wherein the the top part further comprises a filter for protecting against aerosols.

3. The reaction unit according to claim 1, further comprising a support material for binding biomolecules on the permeable filter grid of the bottom part.

4. The reaction unit according to claim 3, wherein the support material is a fiberglass web, a membrane or a chromatographic filter material.

5. The reaction unit according to claim 3, wherein the support material is fixed on the permeable filter grid by combination of the top part onto the bottom part.

6. The reaction unit according to claim 1 wherein the bottom part is a pipette tip.

7. A nucleic acid extraction machine, comprising at least one reaction unit according to claim 1.

8. The extraction machine according to claim 7, which further comprises a bench top device containing a kinematic unit with four degrees of freedom that moves the magnet, a dosing head, a manually-loadable tray, and (i) a suction device or (ii) a compressed air device.

9. The extraction machine according to claim 8, wherein the (i) suction device or (ii) compressed air device is coupled to a dispensing head which is exactly adjusted to the reaction unit.

10. The extraction machine according to claim 8, wherein the compressed air device comprises a heat source.

11. The extraction machine according to claim 8, wherein the kinematic unit for vertical movement of the magnet is located in the dispensing head.

12. The extraction machine according to claim 8, which comprises an interface for communication with a computer for controlling the nucleic acid separation process.

13. A method for the isolation and purification of a nucleic acid from a complex starting material in the reaction unit according to claim 1, comprising:
    lysis of the starting material,
    binding of the nucleic acid to magnetic particles, to obtain a bound nucleic acid and, optionally, filtration of undissolved components,
    washing and drying of the bound nucleic acid, and
    elution of the bound nucleic acid, to obtain said nucleic acid.

14. The method according to claim 13, wherein, before lysis of the starting material, a reaction vessel is filled with a buffer from a reservoir vessel using said reaction unit.

15. The method according to claim 14, wherein the filling of the reaction vessel takes place starting with a solution with the smallest concentration of salt.

16. The method according to claim 15, wherein the filling of the reaction vessel is carried out in the order of:
    first: elution agent, second: washing buffer and third: lysis buffer.

17. The method according to claim 13, wherein the lysis of the sample is carried out by repeated, continuous pipetting in and out of a lysis additive using the reaction unit.

18. The method according to claim 13, wherein after lysis, uptake of the binding buffer and magnetic particle takes place by using the reaction unit, followed by transfer of the binding buffer and the magnetic particles into a lysis additive.

19. The method according to claim 13, wherein a lysis binding buffer additive and the magnetic particles are mixed using the reaction unit by pipetting in and out.

20. The method according to claim 13, wherein the binding of the nucleic acid to the magnetic particles and subsequent filtration of undissolved components as well as magnetic separation comprise:
    absorbing a sample from the bottom part of the reaction unit, over the filter grid, into the top part of the reaction unit,
    moving a magnet out of a dispensing head into the covering or cavity of the top part of the reaction unit,
    returning said sample liquid, without nucleic acids bound to the magnetic particles, into a starting vessel.

21. The method according to claim 13, wherein the washing of the nucleic acid bound to the magnetic particles comprises:
    transferring of a dispensation unit with the reaction unit to a next row of reaction vessels containing a washing buffer,
    subsequently, immersing the reaction unit into a reaction vessel containing said washing buffer and absorbing of the washing buffer up into the top part of the reaction unit,
    removing the magnet, and
    at least two repetitions of the washing and magnet removal.

22. The method according to claim 21, wherein the transferring of the dispensation unit takes place either by incremental movement of the dispensing head or by the incremental movement of a reaction vessel.

23. The method according to claim 13, wherein the drying of the nucleic acid bound to the magnetic particles comprises:
    transferring of the reaction unit to an empty reaction vessel,
    applying compressed air which is optionally heated, and
    flowing of the compressed air over the magnetic particles fixed magnetically to the covering or cavity.

24. The method according to claim 13, wherein the elution of the bound nucleic acid comprises:
- transferring of the dispensing unit with reaction unit to the next row of reaction vessels containing an elution buffer, or transfer of the next row of reaction vessels to an immobile dispensing head,
- immersing of the reaction unit into the reaction vessel with said elution buffer, and absorbing of the elution buffer into the upper part of the reaction unit,
- deploying of the magnet,
- alternately, absorbing and ejecting of the elution buffer, and
- repeating the absorbtion and ejection of the elution buffer.

25. A method for the selective simultaneous isolation of genomic DNA from cellular RNA from a complex starting material in the reaction unit according to claim 1, comprising:
- lysis of the starting material,
- isolation of the genomic DNA, and
- isolation of the RNA.

26. The method according to claim 25, wherein the lysis of the starting material is carried out by repeated, continuing pipetting in and out of a lysis additive using the reaction unit, wherein a glass thread web or a membrane or a chromatographic filter material is located on the filter grid insert.

27. The method according to claim 25, wherein the isolation of the genomic DNA comprises:
- binding of the genomic DNA to the filter grid insert of the reaction unit through multiple, alternating absorption and ejection of a sample from the bottom part of the reaction unit over the filter grid insert into the top part of the reaction unit,
- returning of the lysate with the RNA into the reaction vessel,
- washing of the DNA bound to the filter grid insert, transferring of the reaction unit to the next row of reaction vessels containing a washing buffers,
- immersing the reaction unit in a reaction vessel with said wash buffer, and passing the wash buffer from the bottom part of the reaction unit over the filter grid insert into the top part of the reaction unit by alternate absorption and ejection of the wash buffer,
- returning the washing buffer into the reaction vessel,
- drying of the filter grid insert by application of compressed air which is optionally heated while the reaction unit is located over an empty reaction vessel,
- eluting of the bound DNA by immersion of the reaction unit into a reaction vessel containing elution buffer and alternate absorption and ejection of the elution buffer from the bottom part of the reaction unit over the filter grid insert into the top part of the reaction unit, and transferring of the reaction unit to the next row of reaction vessels containing an elution buffer.

28. The method according to claim 25, wherein the isolation of the RNA comprises:
- setting optimal binding conditions for RNA,
- adding an alcoholic binding buffer and magnetic particles into a remaining lysis additive,
- pipetting a lysis buffer / binding buffer additive using the reaction unit in and out, to mix the lysis buffer / binding buffer additive and the magnetic particles with the reaction unit,
- binding the RNA to the magnetic particles by absorption of the sample from the bottom part of the reaction unit into the top part of the reaction unit,
- magnetic separation of the bound RNA from the sample by movement of the magnet out of the dispensing head into the covering or cavity of the top part of the reaction unit,
- returning of the sample, without the bound RNA, into a starting vessel,
- washing, drying and eluting of the RNA bound to the magnetic particles.

29. The methods according to claim 13 or 26, wherein after lysis, no more liquid handling is performed.

30. The reaction unit according to claim 1, wherein the permeable filter grid insert separates the reaction cavity of the lower part from the reaction cavity in the top part.

31. The reaction unit of claim 30, wherein said reaction unit contains a single top part containing a single reaction cavity and a single bottom part containing a single reaction cavity.

32. A reaction system comprising the reaction unit of claim 30, and further comprising
- magnetic particles, and
- the magnet configured to fit within the cavity or covering of said top part of the reaction unit.

* * * * *

UNITED STATES PATENT AND TRADEMARK OFFICE
CERTIFICATE OF CORRECTION

| | | |
|---|---|---|
| PATENT NO. | : 8,597,878 B2 | Page 1 of 1 |
| APPLICATION NO. | : 12/115766 | |
| DATED | : December 3, 2013 | |
| INVENTOR(S) | : Timo Hillebrand et al. | |

It is certified that error appears in the above-identified patent and that said Letters Patent is hereby corrected as shown below:

On the title page, Item (73), the Assignees' Information is incorrect. Item (73) should read:

--(73) Assignees: AJ Innuscreen GmbH, Berlin (DE);
AJ Cybertron Gesellschaft fuer
Laborautomationssysteme Mbh, Berlin (DE)--

Signed and Sealed this
Eighteenth Day of February, 2014

Michelle K. Lee
*Deputy Director of the United States Patent and Trademark Office*